United States Patent [19]
Capistrano

[11] Patent Number: 5,360,003
[45] Date of Patent: Nov. 1, 1994

[54] INTUBATION ASSEMBLY AND METHOD OF INSERTING SAME HAVING A BALLOON TO INDICATE THE POSITION OF TUBE INSIDE OF THE PATIENT

[76] Inventor: Cecilio L. Capistrano, 809 New Albany Rd., Moorestown, N.J. 08057

[21] Appl. No.: 75,737

[22] Filed: Jun. 11, 1993

[51] Int. Cl.⁵ .................. A61M 16/00; A62B 9/00; A62B 27/00; G08B 3/00
[52] U.S. Cl. .................. 128/207.15; 128/912; 128/202.22; 604/100
[58] Field of Search .................. 128/200.24, 200.26, 128/202.22, 205.23, 207.14–207.18, 911, 912, DIG. 26; 604/100

[56] References Cited

U.S. PATENT DOCUMENTS

| | | | |
|---|---|---|---|
| 2,638,096 | 5/1953 | Waldhaus | 128/202.22 |
| 3,794,043 | 2/1974 | McGinnis | 137/525 |
| 3,848,605 | 11/1974 | Harautuneian | 128/207.15 |
| 4,098,271 | 7/1978 | Maddock | 128/202.22 |
| 4,134,407 | 1/1979 | Elam | 128/202.22 |
| 4,149,556 | 4/1979 | Schwabe | 128/202.22 |
| 4,691,701 | 9/1987 | Williams | 128/207.14 |
| 4,751,924 | 6/1988 | Hammerschmidt et al. | 128/207.15 |
| 4,879,999 | 11/1989 | Leiman et al. | 128/207.14 |
| 4,928,687 | 5/1990 | Lampotang et al. | 128/200.26 |
| 5,134,996 | 8/1992 | Bell | 128/207.14 |

*Primary Examiner*—Kimberly L. Asher
*Attorney, Agent, or Firm*—Oblon, Spivak, McClelland, Maier & Neustadt

[57] ABSTRACT

The present invention relates to a balloon-equipped intubation assembly and to a method of inserting the same into the air passages of a subject. In a particular embodiment of the present invention, an intubation assembly is provided which comprises an endotracheal tube that is equipped, at its proximal end, with a removable balloon adapter. The balloon adapter and its characteristic movements during "blind" intubation are used to monitor the progress of the insertion and ensure its proper positioning within the trachea of the subject.

14 Claims, 5 Drawing Sheets

5,360,003

INTUBATION ASSEMBLY AND METHOD OF INSERTING SAME HAVING A BALLOON TO INDICATE THE POSITION OF TUBE INSIDE OF THE PATIENT

1. FIELD OF THE INVENTION

The present invention relates to medical devices. In particular, the present invention relates to a balloon-equipped intubation assembly comprising an endotracheal tube and a removable balloon adapter. The balloon portion of the adapter is preferably made of an elastic thin-walled material whose movements would be highly sensitive to the air pressure variations encountered during the intubation procedure. Thus, the present invention is also directed to a method of inserting an endotracheal tube into the air passages of a subject. In particular, the balloon adapter and its characteristic movements during the "blind" insertion of the intubation assembly are used to monitor the progress of the intubation and to ensure the proper positioning of the endotracheal tube within the trachea of the subject. The present device and insertion technique thus provide a visual aid to the medical practitioner which is particularly advantageous during blind nasotracheal intubation.

2. BACKGROUND OF THE INVENTION

The endotracheal tube, used to ensure adequate oxygenation (i.e., ventilation) of a conscious or unconscious patient, is a mainstay of internal medicine. Various improvements of the basic endotracheal tube have been described in the literature, including the addition of an inflatable cuff that encircles the distal end of the tube to assist in holding the tube in place within the trachea of the patient. (See, for example, U.S. Pat. No. 3,794,043 granted to McGinnis, which also describes means for inflating the cuff externally and a separate inflatable member that allows the medical practitioner to gauge the pressure of the internal cuff to avoid pressure necrosis of the involved tissues of the trachea.) Other improvements of the endotracheal tube have been described. (See, for example, U.S. Pat. No. 3,848,605 granted to Harautuneian and Penny; U.S. Pat. No. 4,134,407 granted to Elam; and, more recently, U.S. Pat. No. 4,751,924 granted to Hammerschmidt and Zumbruch).

The intubation or insertion of an endotracheal tube into a patient to supplement, assist, or dislace a patient's normal breathing is a common medical procedure that is performed in many settings, including an accident scene, in a rescue vehicle or ambulance, in an emergency room, or a regular operating room. Thus, it is not that unusual for the site in which the procedure is being attempted to be bustling with medical and rescue personnel, along with the noise caused by their vehicles or equipment, not to mention the general pandemonium caused by the people, themselves, shouting and yelling instructions to one another.

It is under such circumstances that the medical practitioner frequently has to perform the intubation procedure. Typically, the endotracheal tube is inserted intraorally, if the patient is unconscious. (If the patient is conscious or has an intact gag reflex, then the tube is inserted intranasally to provide more comfort for the patient).To verify proper insertion, the medical practitioner will typically do one of two things: first, he or she may place the proximal end of the tube to his or her ear to listen for the sounds made by the patient's breathing; or, second, he or she may place the end of the tube close to the bottom portion of his or her forearm or wrist in an attempt to feel the movement of air.

All the while, there is the possibility that the patient may cough, sneeze, excrete or, otherwise, expel aerosols, saliva, mucus, and other bodily excretions, especially through the tube and, hence, into the medical practitioner's ear or against his or her exposed skin. What is more, the patient may be suffering from a communicable disorder borne by some microbial, fungal, or viral disease-causing agent. Thus, there is clearly a need for a means by which the medical practitioner can perform and verify a successful intubation without reliance on his or her auditory or hearing acuity or skin sensitivity.

Yet, while the intubation procedure may be extremely difficult in an emergency setting, this common procedure can be quite tricky even in the relative "quiet" of an operating room in the absence of sophisticated fiber viewing optics (e.g., a laryngoscope) that allow the medical practitioner to determine by internal visualization the proper passage into which the endotracheal tube is to be inserted. Such a "blind" insertion (i.e., without the optics) has in the past been aided by use of one of two devices. The first is a whistling device that produces a sound that is created by the rapid passage of air through the device. Unfortunately, such a device is of no help if the patient is in acute respiratory distress (in which case the patient is hardly breathing, if at all), cardiac arrest, or if the patient's breathing is otherwise very shallow or intermittent.

A second device consists of a color change monitor that attaches to the proximal end of the endotracheal tube after intubation. If the distal end of the endotracheal tube is positioned in the trachea, carbon dioxide gas which is exhaled by the patient causes the color monitor to exhibit a color reading that is consistent with proper levels of carbon dioxide gas production. If, instead, the endotracheal tube is located in the esophagus, the color reading will reflect inadequate levels of carbon dioxide, and the medical practitioner will then attempt to re-intubate the patient. While providing a visual signal, the color change monitor requires a minimum of six full breaths for an accurate color change to develop (up to 20-25 seconds after the endotracheal tube as hopefully been positioned properly and the air cuff, if equipped, inflated). Besides requiring a relatively extended period for providing a color reading, which approaches the ACLS allowable anoxic intubation time of 30 seconds, the above-mentioned color change monitor requires careful comparison of the various colors that are produced by the device against standard color charts. Moreover, the color change monitor is relatively expensive, adding about $40 to the cost of the procedure.

Hence, there remains a need for providing a simple, quick, and effective means of facilitating the insertion of an endotracheal tube and of verifying proper placement in the trachea of the patient.

3. SUMMARY OF THE INVENTION

Accordingly, the present invention is directed to an intubation assembly comprising an endotracheal tube having proximal and distal ends and an elastic, thin-walled balloon attached to the proximal end of the endotracheal tube. Preferably, the elastic, thin-walled balloon forms part of a balloon adapter. Thus, in one embodiment of the present invention, the balloon adapter comprises (i) an elastic, thin-walled balloon that is visibly responsive to the pressure variations within the air passages of a patient coincident with the inspiratory and expiratory phases of the patient's respiration, and (ii) a hollow cylindrical member, one end of which is connected to the balloon so as to be in fluid communication therewith while the opposite end may be detachably affixed to the proximal end of the endotracheal tube. On blind oral or nasal insertion of the intubation assembly into the air passages of the patient, the characteristic movements of the balloon in response to internal air pressure variations provide a visual indication of the progress of the intubation and the proper positioning of the endotracheal tube in the trachea of the patient.

In another embodiment of the present invention, that end of the cylindrical member, which is detachably affixed to the proximal end of the endotracheal tube, preferably comprises a standard 15/22 fitting, for ease and convenience in affixing the balloon adapter to the proximal end of the endotracheal tube. The cylindrical member may be made of any durable material, including hard plastic or hard rubber. The endotracheal tube, itself, may come in a number of sizes, including one sized for an adult patient and one sized for a pediatric patient. In specific aspects of the invention, the intubation assembly may include an endotracheal tube that has been adapted for intranasal or intraoral insertion. Other modifications will be apparent to one of ordinary skill in the art, such as, for example, the incorporation of a stylet for easier use during intraoral intubation.

It is, thus, an important objective of the present invention to provide an intubation assembly in which the absence of any characteristic movement of the balloon or the singular collapse thereof is an indication that the distal end of the endotracheal tube has been improperly positioned, most likely, having been inserted into the esophagus of a respirating patient. Of critical importance to the present invention is the recognition that a balloon adapter, comprising a sufficiently elastic, thin-walled balloon, can provide a visual indication of the pressure variations within the air passages of a patient during breathing, however shallow, strained or intermittent, particularly with patients in some form of distress. particular, it has been discovered that the characteristic fluttering or quivering movements of the balloon are substantially coincident with and indicative of the inspiratory and expiratory phases of the patient's respiration. As mentioned above, a hollow cylindrical member, one end of which is sealably connected to but in fluid communication with the opening of the balloon while the opposite, open end may be affixed, for example, by sliding or twisting, to the proximal end of an endotracheal tube, is preferably made an integral part of the balloon adapter.

It is, thus, a further object of the present invention to provide a method of "blind" intubation (i.e., without the use of an internal visualization device to assist the medical practitioner in guiding the distal end of the endotracheal tube into the trachea) comprising: (a) inserting an endotracheal tube by its distal end into the air passages of a patient, the endotracheal tube further comprising an elastic, thin-walled balloon detachably affixed to the proximal end of the endotracheal tube, the balloon being visibly responsive to the pressure variations within the air passages of the patient coincident with the inspiratory and expiratory phases of the patient's respiration; (b) observing the characteristic movements of the balloon, including the fluttering, quivering or periodic distention and collapse of same, as a visual indication of the progress of the intubation and positioning of the endotracheal tube about the superior region of the trachea of the patient; (c) further inserting the endotracheal tube through the epiglottis and vocal cords into the trachea of the patient during the collapsed phase of the periodic movements of the balloon, which collapsed phase is coincident with the inspiratory phase of the patient's respiration and the physiological opening the patient's epiglottis and vocal cords; and (d) verifying the position of the endotracheal tube past the epiglottis and vocal cords and within the trachea of the patient as evidenced by a visible increase in the intensity of the characteristic movements of the balloon. The increased intensity may be reflected in a greater magnitude of the distention of the balloon. After proper intubation has been verified, the balloon is then detached from the endotracheal tube, and the patient is ventilated normally.

In the above-described method, the medical practitioner may rely on the characteristic fluttering of the balloon, which fluttering would be absent if the distal end of the endotracheal tube is positioned in the esophagus of a respirating patient. Preferably, the intubation assembly used in the method includes a hollow cylindrical member, one end of which is sealably connected to but in fluid communication with the opening of the balloon while the opposite end is detachably affixed to the proximal end of the endotracheal tube. According to the needs of the patient, the endotracheal tube may either be inserted intranasally or intraorally. Preferably, the patient is first placed in a sniffing position, prior to the initiation of the intubation procedure.

These and other objects of the present invention will be apparent to those of ordinary skill in the art especially in view of the figures and additional detailed description.

4. BRIEF DESCRIPTION OF THE DRAWINGS

FIG. 1 is an illustration of the structure of the upper respiratory tract.

FIG. 2A is an illustration of the balloon adapter (10) of the present invention, here shown with a standard 15/22 fitting. This standard-sized fitting is suitably affixable to the proximal end of a standard endotracheal tube (11). As clearly indicated in this figure, the balloon adapter comprises a means for indicating the position of the distal end of the endotracheal tube, said means comprising an elastic, thin-walled inflatable balloon portion and a connector portion being the sole means for entry of air into the balloon portion. The connector portion comprises a hollow cylindrical member having a first end circumferentially sealed to said balloon portion and a second end adapted for connection to the proximal end of said endotracheal tube.

FIG. 3B is an illustration of a second existing technique in which the proximal end of the endotracheal tube is placed against the skin, which, again, exposes the medical practitioner to possible "sick air" that could be contaminated with the AIDS virus, Rhinoviruses, tuberculosis, pneumococcus, bacteria, fungi, and the like.

Figure 4A:
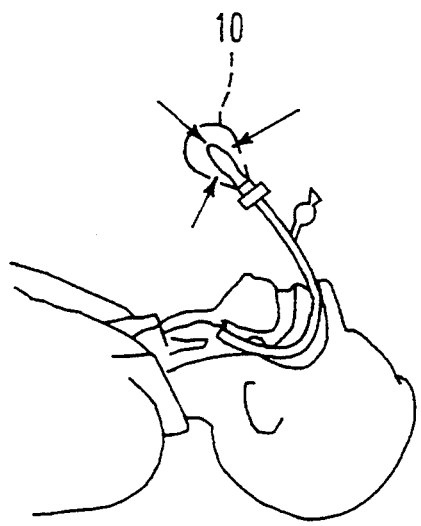
Figure 4B:
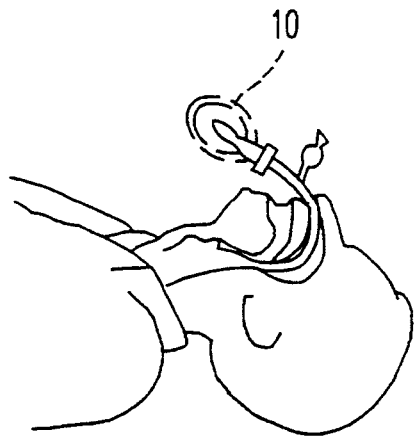
Figure 4C:
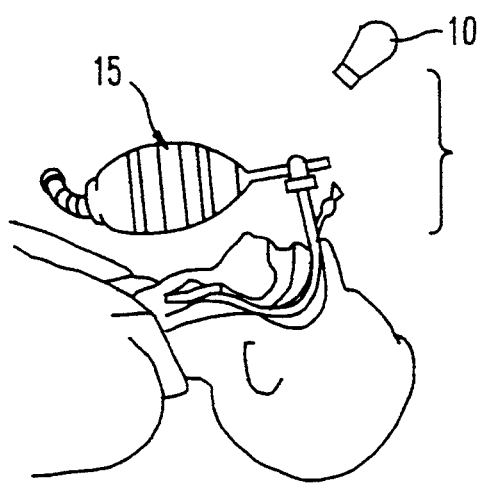

FIGS. 4A–4C illustrate the serial stages in which the balloon equipped intubation assembly of the present invention is inserted intranasally. In FIG. 4A, the balloon is observed to collapse, coincident with inspiration and providing an indication of proper timing for further insertion of the tube down the patient's vocal cords. In FIG. 4B, the periodic distention and collapse of the balloon is indicative of the rhythmic pattern of respiration and, thus, proper insertion within the trachea. In FIG. 4C, the balloon adapter (10) is removed easily and replaced by an AMBU BAG ™ (15).

Figure 5:
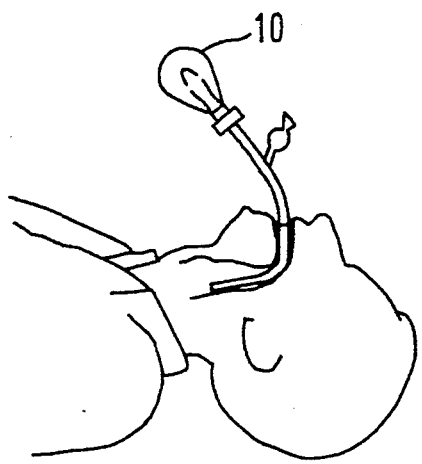

FIG. 5 illustrates the intraoral insertion of the intubation assembly of the present invention.

DESCRIPTION OF THE PREFERRED EMBODIMENTS

The present invention offers a positive visual verification of the progress of intubation and proper positioning of the endotracheal tube in the trachea of the patient. This visual verification is simple and independent of the medical practitioner's hearing acuity or skin sensitivity. Moreover, in actual use, it has been found that the present invention can provide a rapid indication of proper tracheal placement of the endotracheal tube, requiring no more than about a five second confirmatory period after the intubation attempt. Additionally, the present technique spares the medical practitioner from being inappropriately exposed to a patient's aerosols, bodily fluids, or other excretions.

Figure 1:
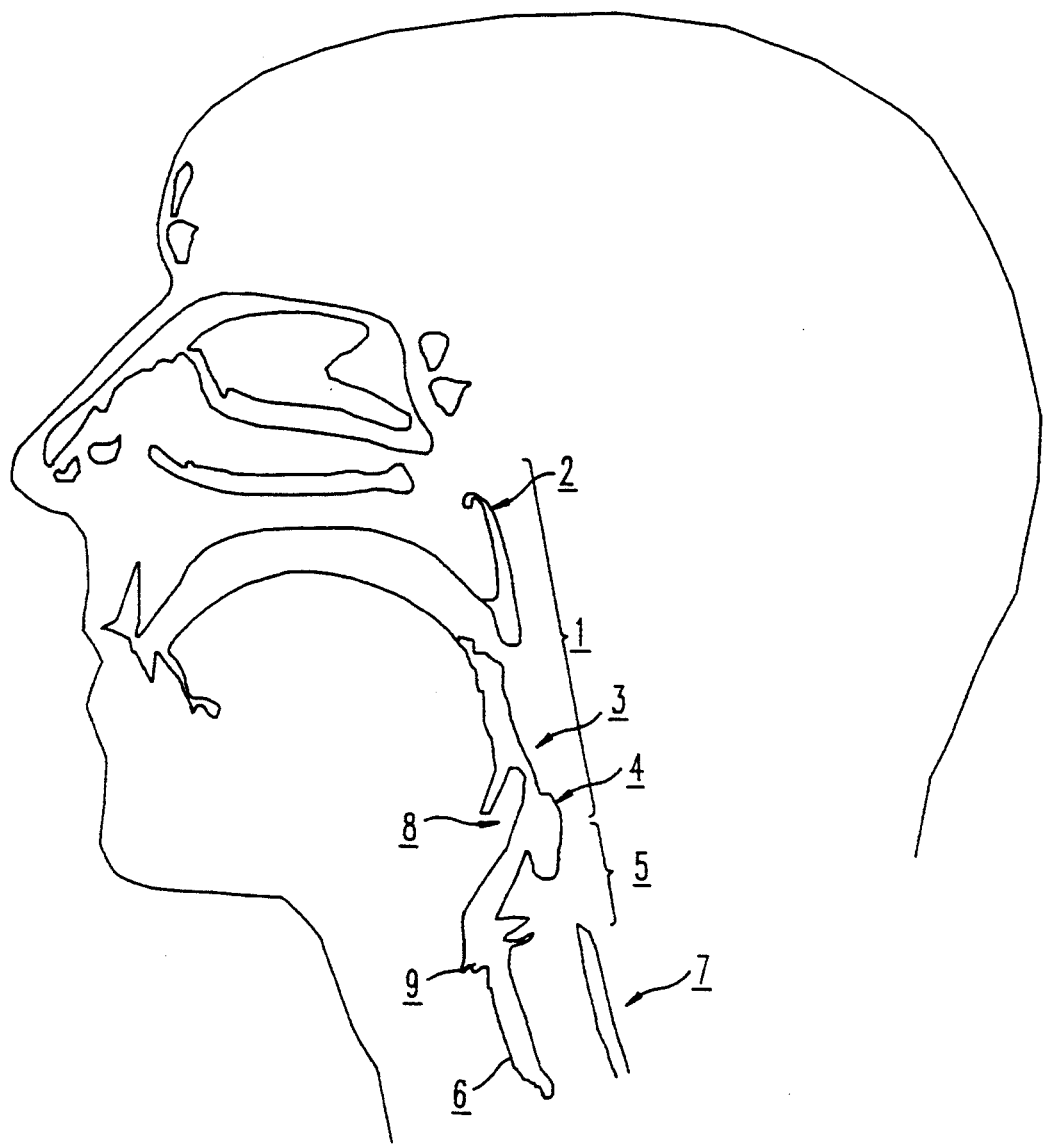

The objects of the present invention are better understood with reference to the figures. Hence, FIG. 1 is an illustration of the structure of the upper respiratory tract, including the pharynx (1), which consists of the nasopharynx (2), the oropharynx (3), and the laryngopharyn or hypopharynx (4), and the larynx (5), which connects superiorly with the laryngopharynx and continues inferiorly into the trachea (6). The trachea, of course, leads to the lower respiratory tract and lungs. Also, shown are the esophagus (7), located posterior to the trachea and leading to the stomach and other organs of the digestive tract; the epiglottis (8), which covers the opening to the trachea during swallowing; and the vocal cords (9), located above the trachea. During the inspiratory phase of a person's breathing (i.e., when inhaling), both the epiglottis and vocal cords are open.

Figure 2A:
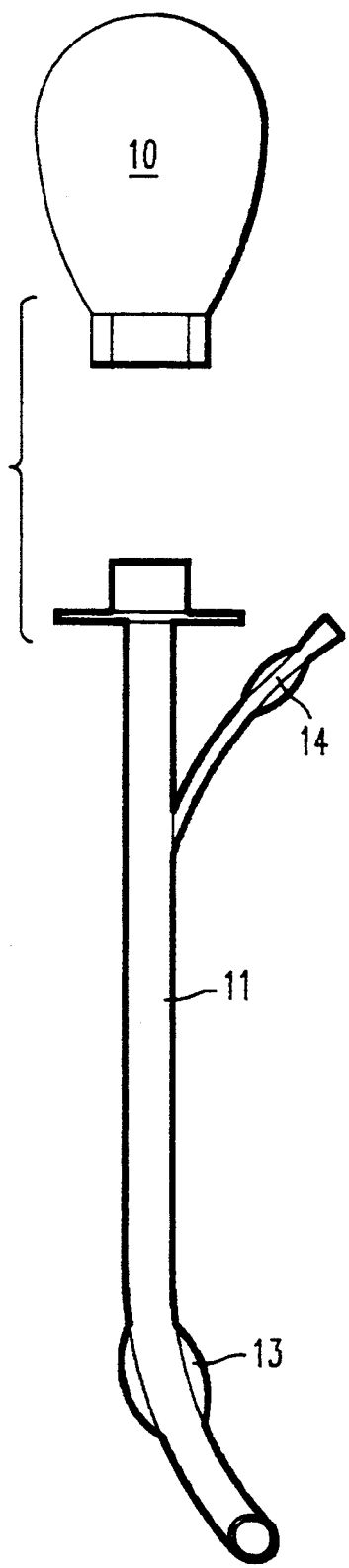
FIG. 2B illustrates the balloon adapter affixed to the end of an endotracheal tube to form the new assembly (12).
Figure 2B:
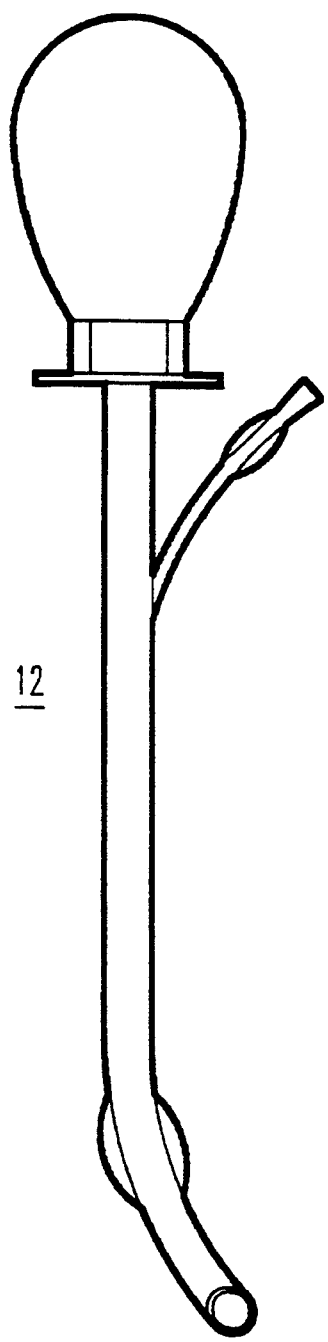

FIG. 2 is an illustration of the balloon adapter (10) of the present invention, which together with an endotracheal tube (11) comprises the balloon-equipped intubation assembly (12). Note that most endotracheal tubes also come equipped with an air cuff (13) circumscribing the distal end of the endotracheal tube. After the endotracheal tube is inserted in the trachea, the distal air cuff is inflated to "lock" the endotracheal tube against the walls of the trachea and to prevent air "leakage" around the tube. The air pressure inside the distal air cuff may be gauged by the "hardness" of a separate inflatable member (14) that is connected via a separate tubing to the distal air cuff. The separate inflatable member (14) is located outside the patient at all times. Both this distal air cuff and the separate inflatable member form no part of the present invention.

Therefore, the preferred intubation assembly of the present invention may be inserted intranasally or intraorally into the air passages of a patient requiring air ventilation, passing first through the nasopharynx, then the oropharynx, and then the laryngopharynx. On entering the region of the larynx, the distal end of the tube may be inserted further into the patient. However, the tube has two anotomical openings in which to enter: one is the esophagus, which leads to the stomach; the other, desired opening is through the vocal cords and into the trachea. It should be noted that especially with pediatric patients, the distal end of the endotracheal tube can enter the esophagus just as easily as the trachea. Moreover, if the epiglottis is "closed," then the opening to the trachea is blocked.

Figure 3B:
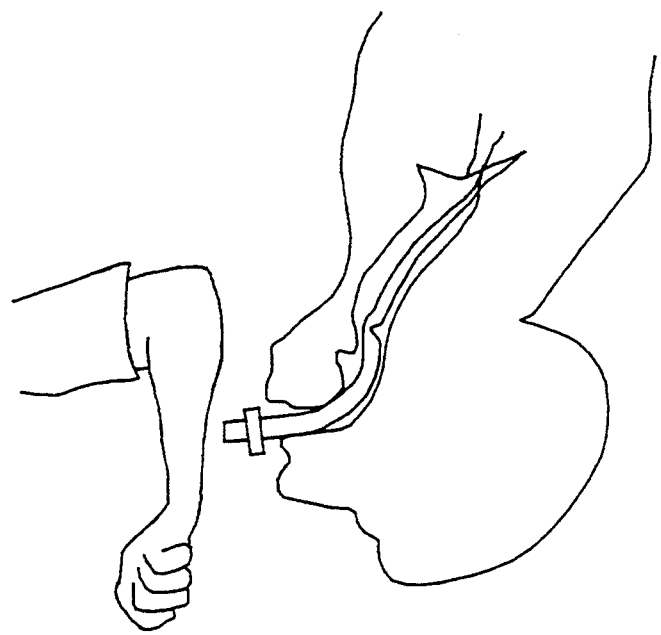
Figure 3A:
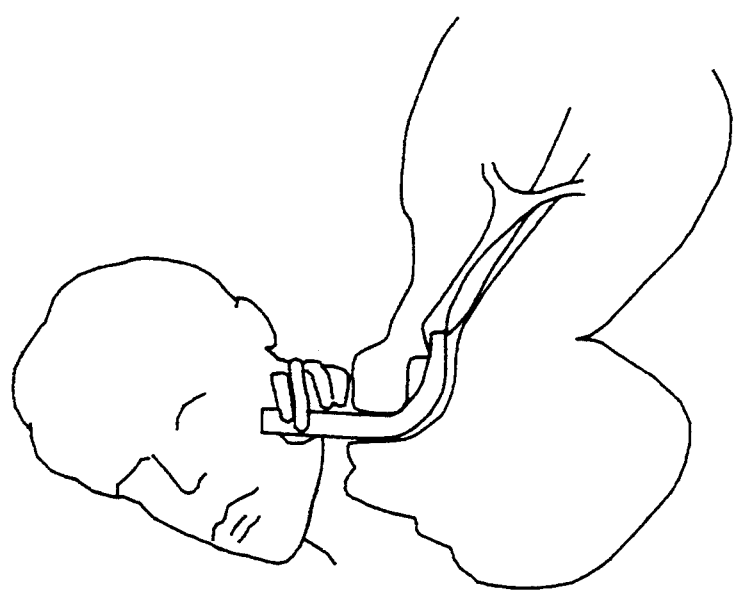
FIG. 3A is an illustration of an existing technique for determining the proper positioning of an endotracheal tube in which the medical practitioner is at risk of receiving a burst or a bolus of secretion directly into his/her ear.

FIG. 3A is an illustration of an existing technique for determining the proper positioning of an endotracheal tube; that is, the medical practitioner holds the proximal end of the endotracheal tube against his ear to listen for the sounds of respiration or airflow. Unfortunately, in a noisy emergency room setting or accident scene, it is not always that easy to listen for the subtle sounds of respiration. FIG. 3B is an illustration of a second existing technique in which the proximal end of the endotracheal tube is placed against the skin, such as against the bottom part of the forearm or wrist. The success of this technique depends on the ability of the medical practitioner to sense the airflow emerging from the tube. Again, this approach can be hindered both by the sensitivity of the skin and clothing.

FIG. 4A–C illustrate the serial stages in which the balloon-equipped intubation assembly of the present invention is inserted intranasally until the distal end is located in the larynx, approximately superior to the epiglottis and vocal cords (FIG. 4A). Almost upon insertion into the air passages of the patient, the elastic, thin-walled balloon begins to quiver and flutter in response to the changes in the internal air pressure within the upper respiratory tract. The elastic, thin walled balloon may be made of any distendable material, such as rubber, latex or thin plastic, so long as the balloon is responsive to low pressure, preferably providing a conspicuous volume even at low pressure.

The periodic movements (distention and collapse) of the elastic, thin-walled balloon is then used advantageously, such that further timely insertion of the distal end through the epiglottis and vocal cords and into the trachea is made coincident with the collapsed (inspiratory) phase of the elastic, thin-walled balloon (FIG. 4B). Proper positioning within the trachea is then verified by the more vigorous distention and collapse of the elastic, thin-walled balloon reflective of the constricted air passage through the trachea, especially if the endotracheal tube is further equipped with a distal air cuff. The characteristic movements of the balloon are rhythmic with the patient's respiration. Finally, FIG. 4C illustrates the step in which the balloon adapter (10) of the present invention is removed from the properly inserted endotracheal tube and replaced by a conventional Ambu Bag ™ adapter (15) for ventillating the patient in the usual manner.

Numerous types of patient would benefit from the present balloon-equipped intubation assembly and preferred nasotracheal insertion technique. Such patients include, but are not limited to, those who are conscious (or have some level of responsiveness) and have an itact respiratory effort but suffering from some form of respiratory distress (e.g., decompensated chronic obstructive pulmonary disease, decompensated asthma, severe congestive heart failure, pulmonary edema, and the like) requiring ventilation support. Other patients may have an impaired central nervous system, either through disease, accident, or drug overdose. In addition, nasotracheal intubation may be the preferred route during oral surgical procedures for control of the airway for administering anesthesia or for anticipated and prolonged tracheal intubation. The preferred nasotracheal intubation, may also be made necessary by pre-existing physical conditions of the patient, such as a large tongue size, small mandibular space, or restricted atlanto-occipital extension. As mentioned previously, the patient is preferably first placed in the conventional sniffing position.

5. EXAMPLE

The following detailed procedure is exemplary of the present invention but not meant to be limiting thereof.

An HIV-positive patient suffering from acute pulmonary distress and requiring immediate assistance with breathing was brought into the emergency room. First, the patient was pre-oxygenated prior to intubation with a conventional masked oxygenation device (e.g., an AMBU BAG TM. Next, a suitable tube size was selected. In this case, as with most adult patients, a tube having a 7.0–7.5 mm internal diameter was chosen. The tube was then lubricated prior to insertion. (The lubricant is preferably a jelly, such as Lidocaine.).

Next, the patient's nasal mucosa was anesthetized and shrunk with the use of a cocaine nasal spray. (Alternatively, one can also use phenylephrine spray to shrink the mucosa.) Optionally, the medical practitioner may then perform a digital examination of the nasal passages. The endotracheal tube was then inserted gently, with the axis of the tube preferably perpendicular to the axis of the patient's head. Applying a gradual steady downward pressure during insertion, one observed the periodic collapse and distention of the elastic, thin-walled balloon with each respiratory movement of the patient.

As stated previously, insertion is best carried out while the patient is in a sniffing position: That is, if the patient is reclined on a stretcher, the patient's head and the back rest of the stretcher should be inclined upward about thirty degrees from the horizontal axis. A soft, rolled up material, such as a towel, is preferably placed underneath the patient's occiput, and the patient's chin is lifted upward.

Pushing the tube still further down, one continued to observe the periodic motions of the balloon until one sensed that the distal end of the endotracheal tube was at about the area of the larynx, just superior to the vocal cords. During the collapsed phase of the balloon (when the patient is in an inspiratory phase and which phase coincides with the physiological opening of the epiglottis and vocal cords), the tube was pushed down past the epiglottis and vocal cords.

Once past the vocal cords, one observed a marked increase in the degree or magnitude of the characteristic movements of the balloon. This greater distention and more vigorous collapse signaled the proper positioning of the tube at the respiratory tree (i.e., in the patient's trachea). No movement would have been detected if the distal end of the endotracheal tube had been located incorrectly in the patient's esophagus. Subsequently, the balloon or adapter device was disengaged from the endotracheal tube, and the patient was ventilated in the usual intended mode.

Other embodiments of the present invention will be apparent to one of ordinary skill in the art, which embodiments would not lie outside the scope and spirit of the present invention. Hence, the present invention should not be limited to the specific embodiments disclosed herein, but only by the claims that follow.

What is claimed is:

1. An intubation assembly comprising an endotracheal tube having proximal and distal ends and a balloon adapter attached to said proximal end of said endotracheal tube, said balloon adapter comprising means for indicating the position of said distal end of said endotracheal tube inserted into a patient, said means comprising an elastic, thin-walled inflatable balloon portion and a connector portion, said connector portion being the sole means for entry of air into said balloon portion, said connector portion comprising a hollow cylindrical member having a first end circumferentially sealed to said balloon portion and a second end adapted for connection to said proximal end of said endotracheal tube, said balloon adapter indicating the location of said distal end of said endotracheal tube by the expansion and contraction of said balloon portion with the expiration and inspiration, respectively, of the patient upon insertion of said distal end of said endotracheal tube into the opening of the patient's trachea, said balloon portion indicating placement of said distal end of said endotracheal tube past the vocal cords and within the trachea upon increased intensity of the inflation and deflation of said balloon portion.

2. The intubation assembly of claim 1 in which the second end of the cylindrical member, adapted for connection to said proximal end of said endotracheal tube, comprises a standard 15/22 fitting.

3. The intubation assembly of claim 1 in which said endotracheal tube is sized for an adult patient.

4. The intubation assembly of claim 1 in which said endotracheal tube is sized for a pediatric patient.

5. A balloon adapter for attachment to a proximal end of an endotracheal tube having proximal and distal ends, said adapter comprising means for indicating the position of said distal end of said endotracheal tube inserted into a patient, said means comprising an elastic, thin-walled inflatable balloon portion and a connector portion, said connector portion being the sole means for entry of air into said balloon portion, said connector portion comprising a hollow cylindrical member having a first end circumferentially sealed to said balloon portion and a second end adapted for connection to said proximal end of said endotracheal tube, said balloon adapter indicating the location of said distal end of said endotracheal tube by the expansion and contraction of said balloon portion with the expiration and inspiration, respectively, of the patient upon insertion of said distal end of said endotracheal tube into the opening of the patient's trachea, said balloon portion indicating placement of said distal end of said endotracheal tube past the vocal cords and within the trachea upon increased intensity of the inflation and deflation of said balloon portion.

6. A method of blind intubation comprising:
(a) providing an endotracheal tube having proximal end distal ends and an elastic, thin-walled balloon detachably affixed to the proximal end of said endotracheal tube, said balloon being visibly responsive to the pressure variations within the air passages of a patient coincident with the inspiratory and expiratory phases of the patient's respiration;

(b) inserting said endotracheal tube by its distal end into the air passages of a patient;

(c) observing movements of said balloon to determine the location of the distal end of said endotracheal tube wherein the periodic distention and collapse of said balloon is a visual indication of impending tracheal placement;

(d) after observing said visual indication of impending tracheal placement of said endotracheal tube, further inserting said endotracheal tube into the trachea of the patient during the collapsed phase of said balloon, which collapse is coincident with the inspiratory phase of the patient's respiration and opening of the patient's epiglottis and vocal cords; and (e) verifying the position of the endotracheal tube past the vocal cords and within the trachea of the patient as evidenced by a visible increase in the intensity of the characteristic movements of said balloon.

7. The method of claim 6 which further comprises detaching said balloon from said endotracheal tube and allowing the patient to be ventilated by conventional means.

8. The method of claim 6 which further comprises monitoring said characteristic movements, including a fluttering of said balloon, which fluttering would be absent if the distal end of said endotracheal tube is positioned in the esophagus of a respirating patient.

9. The method of claim 6 which further comprises equipping said balloon with a hollow cylindrical member, one end of which is sealably connected to and in fluid communication with said balloon, while the opposite end is detachably affixed to the proximal end of said endotracheal tube.

10. The method of claim 6 in which step (a) comprises inserting said endotracheal tube intranasally.

11. The method of claim 6 in which step (a) comprises inserting said endotracheal tube intraorally.

12. The method of claim 6 which further comprises sizing said endotracheal tube for an adult patient.

13. The method of claim 6 which further comprises sizing said endotracheal tube for a pediatric patient.

14. The method of claim 6 which further comprises placing said patient in a sniffing position before performing step (a).

* * * * *